(12) United States Patent
Tubo et al.

(10) Patent No.: US 11,857,576 B2
(45) Date of Patent: Jan. 2, 2024

(54) COMPOSITIONS AND METHODS FOR REPAIRING CARTILAGE DEFECTS

(71) Applicant: Vericel Corporation, Cambridge, MA (US)

(72) Inventors: Ross A. Tubo, Douglas, MA (US); Xing Zhao, Lexington, MA (US)

(73) Assignee: Vericel Corporation, Cambridge, MA (US)

( * ) Notice: Subject to any disclaimer, the term of this patent is extended or adjusted under 35 U.S.C. 154(b) by 441 days.

(21) Appl. No.: 16/770,554

(22) PCT Filed: Dec. 7, 2018

(86) PCT No.: PCT/US2018/064629
§ 371 (c)(1),
(2) Date: Jun. 5, 2020

(87) PCT Pub. No.: WO2019/113558
PCT Pub. Date: Jun. 13, 2019

(65) Prior Publication Data
US 2021/0052661 A1   Feb. 25, 2021

Related U.S. Application Data

(60) Provisional application No. 62/596,009, filed on Dec. 7, 2017.

(51) Int. Cl.
| A61K 35/32 | (2015.01) |
| A61L 27/24 | (2006.01) |
| A61L 27/38 | (2006.01) |

(52) U.S. Cl.
CPC .............. *A61K 35/32* (2013.01); *A61L 27/24* (2013.01); *A61L 27/3817* (2013.01); *A61L 2430/06* (2013.01); *A61L 2430/24* (2013.01)

(58) Field of Classification Search
None
See application file for complete search history.

(56) References Cited

U.S. PATENT DOCUMENTS

| 6,547,719 B1 * | 4/2003 | Atala ................. A61L 27/18 623/23.65 |
| 2003/0012805 A1 * | 1/2003 | Chen .................. A61L 27/48 435/399 |
| 2003/0211604 A1 * | 11/2003 | E. Brown ............ C12N 5/0655 435/366 |
| 2008/0268053 A1 | 10/2008 | Geistlich et al. |
| 2009/0016997 A1 | 1/2009 | Hathaway et al. |
| 2009/0186062 A1 * | 7/2009 | Spector ................ A61L 31/005 424/423 |
| 2011/0274729 A1 | 11/2011 | Collins |
| 2012/0230966 A1 * | 9/2012 | Crawford ............... A61K 35/28 435/325 |
| 2013/0226314 A1 * | 8/2013 | Li ......................... A61L 31/14 427/2.24 |
| 2017/0100434 A1 * | 4/2017 | Majumdar ........... C12N 5/0669 |

FOREIGN PATENT DOCUMENTS

| WO | WO-2006/008748 A2 | 1/2006 |
| WO | WO-2012/158952 A1 | 11/2012 |
| WO | WO-2019/113558 A1 | 6/2019 |

OTHER PUBLICATIONS

Alsalameh, S. et al., Antigenicity and accessory cell function of human articular chondrocytes, J Rheumatol, 18(3):414-21 (1991).
Abe, S. et al., Alloreactivity and immunosuppressive properties of articular chondrocytes from osteoarthritic cartilage, J Orthop Surg (Hong Kong), 24(2):232-9 (2016).
Adkisson, H.D. 4th et al., The potential of human allogeneic juvenile chondrocytes for restoration of articular cartilage, Am J Sports Med, 38(7):1324-33 (2010).
Cheuk, Y. C. et al., Use of allogeneic scaffold-free chondrocyte pellet in repair of osteochondral defect in a rabbit model, J Orthop Res, 29(9):1343-50 (2011).
Frisbie, DD et al., A comparative study of articular cartilage thickness in the stifle of animal species used in human pre-clinical studies compared to articular cartilage thickness in the human knee, Vet Comp Orthop Traumatol, 19(3):142-6 (2006).
Huey, D. J. et al., Immunogenicity of bovine and leporine articular chondrocytes and meniscus cells, Tissue Eng Part A, 18(5-6):568-75 (2012).
HYC, A. et al., Immunological response against allogeneic chondrocytes transplanted into joint surface defects in rats, Cell Transplant, 6(2):119-24 (1997).
International Search Report for PCT/US2018/064629 (Compositions and Methods for Repairing Cartilage Defects, filed Dec. 7, 2018), issued by ISA/US, 3 pages (dated Mar. 21, 2019).
Lohan, P. et al., Culture expanded primary chondrocytes have potent immunomodulatory properties and do not induce an allogeneic immune response, Osteoarthritis Cartilage, 24(3):521-33 (2016).
Pereira, R. C. et al., Human articular chondrocytes regulate immune response by affecting directly T-cell proliferation and indirectly inhibiting monocyte differentiation to professional antigen-presenting cells, Front Immunol, 24(7):415 (2016).
Shangkai, C. et al., Transplantation of allogeneic chondrocytes cultured in fibroin sponge and stirring chamber to promote cartilage regeneration. Tissue Eng, 13(3):483-92 (2007).
Standard guide for in vivo assessment of implantable devices intended to repair or regenerate articular cartilage (https://www.astm.org/Standards/F2451.htm).

(Continued)

*Primary Examiner* — Elizabeth C. Kemmerer
(74) *Attorney, Agent, or Firm* — Choate, Hall & Stewart LLP; Peter A. Flynn; Qing Hua Wang

(57) ABSTRACT

The present disclosure provides compositions and methods for repairing cartilage defects.

19 Claims, 2 Drawing Sheets

(56) References Cited

OTHER PUBLICATIONS

Weinand, C. et al., Healing potential of transplanted allogeneic chondrocyte of three different sources in lesions of avascular zone of the meniscus: a pilot study, Arch Orthop Trauma Surg, 126(9):599-605 (2006).

Written Opinion for PCT/US2018/064629 (Compositions and Methods for Repairing Cartilage Defects, filed Dec. 7, 2018), issued by ISA/US, 17 pages (dated Mar. 21, 2019).

Warwick, R. et al., Report of the 17th International Congress of the European Association of Tissue Banks (EATB) held jointly with the 17th Annual Congress of the British Association for Tissue Banking (BATB) including EATB/BATB/American Association of Tissue Banks (AATB) Cardiovascular Symposium, Cell Tissue Bank, 11:107-154 (2010).

Muinos-Lopez, E. et al., Cryopreservation Effect on Proliferative and Chondrogenic Potential of Human Chondrocytes Isolated from Superficial and Deep Cartilage, The Open Orthopaedics Journal, 6:150-159 (2012).

Nixon, A.J. et al., A chondrocyte infiltrated collagen type I/III membrane (MACI implant) improves cartilage healing in the equine patellofemoral joint model, Osteoarthritis and Cartilage, 23:648-660 (2015).

\* cited by examiner

COMPOSITIONS AND METHODS FOR REPAIRING CARTILAGE DEFECTS

RELATED APPLICATIONS

This application is a national stage filing under U.S.C. § 371 of PCT International Application No. PCT/US2018/064629 filed Dec. 7, 2018, which claims the benefit of and priority to U.S. Provisional Application No. 62/596,009, filed Dec. 7, 2017, the disclosure of which is incorporated herein by reference in its entirety.

BACKGROUND

Chondral and osteochondral lesions such as, for example, focal lesions in the load bearing region of a knee's articular cartilage, greatly increase the risk for osteoarthritis. This type of lesion occurs frequently from, for example, trauma, participation in sports, dissecting osteochondritis, etc. The capacity for spontaneous repair of chondral lesions is minimal, due in part to the limited blood supply to cartilage tissue.

Certain current therapeutic intervention strategies typically involve removing damaged or dislodged cartilage from the joint by physical removal and washing via arthroscopy. Such treatments typically provide temporarily relief from symptoms of the injury, but they do not treat the origin of the lesion, or defect, and, in particular do not prevent progressive degradation of the cartilage.

Alternative current therapeutic intervention strategies include total knee replacements, which are sometimes used to treat severe cases of osteoarthritis. However, artificial prostheses have a limited lifespan and thus are not optimal for patients at all ages. Moreover, true treatment of osteoarthritic cartilage degradation requires replacement of defective cartilage with healthy cartilage; autologous chondrocyte implantation strategies have been described to accomplish such replacement. (Brittberg et al. Clin. Orthopaed. Red. Res. (1999) 367S: S147-S155). In such procedures, chondrocytes are harvested from a patient, expanded in cell culture to increase the number of chondrocytes, and then implanted back into the injury site of the patient.

More recent work has improved autologous implantation by seeding expanded autologous cells on a matrix in a process known as matrix-induced autologous chondrocyte implantation (MACI). (Basad et al. In: Hendrich et al., Cartilage Surgery and Future Perspectives, Thieme Verlag, 49-56 (2003)).

SUMMARY

The present disclosure provides important improvements to matrix-induced chondrocyte implantation technologies. For example, among other things, the present disclosure demonstrates feasibility and/or effectiveness of matrix-induced implantation of allogeneic, rather than autologous, chondrocytes. Advantages of provided technologies include, for example, that only a single invasive procedure is required to treat subjects using provided allogeneic chondrocyte compositions. Even MACI implants, which permit treatment of cartilage lesions and defects using minimally invasive interventions, still require at least two interventions, one to harvest autologous cells, and one to administer the implant. Provided technologies, thus, represent and embody further improvements even with respect to MACI technologies.

In some embodiments, the present disclosure provides a composition comprising cultured allogeneic cells grown from a cryogenically frozen cell bank sample and a resorbable collagen membrane, wherein cells are seeded on the membrane at a density of at least 250,000 cells per cm$^2$.

In some embodiments, the present disclosure provides a method of manufacturing an allogeneic cartilage matrix, the method comprising steps of thawing a cryogenically frozen cell bank sample, culturing cells of the sample, characterizing the sample, preparing a resorbable collagen membrane, seeding the membrane with culture, and packaging the membrane.

In some embodiments, the present disclosure provides a composition for use in therapy, wherein the composition comprises cultured allogeneic cells grown from a cryogenically frozen cell bank sample, and a resorbable collagen membrane; wherein the cells are seeded on the membrane at a density of at least 250,000 cells per cm$^2$.

In some embodiments, the present disclosure provides a composition for use in a method of treating a chondral and/or osteochondral defect, wherein the composition comprises cultured allogeneic cells grown from a cryogenically frozen cell bank sample and a resorbable collagen membrane; wherein the cells are seeded on the membrane at a density of at least 250,000 cells per cm$^2$.

In some embodiments, the present disclosure provides a cell bank for use in a method of manufacturing a matrix, wherein the matrix comprises cultured allogeneic cells grown from a cryogenically frozen cell bank sample and a resorbable collage membrane; wherein the cells are seeded on the membrane at a density of at least 250,000 cells per cm$^2$.

In some embodiments, the present disclosure provides a composition for use in a method of treating a chondral defect and/or osteochondral defect, wherein the method comprises implanting a composition comprising cultured allogeneic cells.

In some embodiments, a cryogenic cell bank sample is thawed in a water bath, a heat block, or a dry cell bath at about 37° C.

In some embodiments, a sample is cultured in medium comprising DMEM. In some embodiments, a sample is cultured in medium comprising DMEM, HEPES, Fetal Bovine Serum, and Gentamicin.

In some embodiments, a sample is characterized for viability, presence of viruses, sterility, endotoxin, mycoplasma, senescence, identity, aggrecan, and karyology.

In some embodiments, cells are a monolayer on a membrane.

In some embodiments, cells are dedifferentiated.

In some embodiments, a resorbable collagen membrane comprises type I and type III collagen. In some embodiments, a resorbable collagen membrane comprises porcine collagen. In some embodiments, porcine collagen is derived from a porcine peritoneum.

In some embodiments, the present disclosure provides a method of treating a chondral and/or osteochondral defect in a human subject, the method comprising implanting into the subject a composition provided by the present disclosure.

In some embodiments, a composition comprises dedifferentiated cells.

In some embodiments, a human subject is an adult or juvenile.

In some embodiments, a chondral defect and/or osteochondral defect is in an articulating joint. In some embodiments, an articulating joint is a knee, hip, ankle, elbow, wrist or shoulder.

In some embodiments, a composition is implanted over and/or into a defect.

In some embodiments, a composition is trimmed to a size and/or shape to cover over and/or fit into a chondral and/or osteochondral defect.

In some embodiments, a composition is implanted with at least one surface comprising allogeneic human chondrocytes in contact with a chondral and/or osteochondral defect.

In some embodiments, multiple layers of a composition are implanted over and/or into a defect.

In some embodiments, cells comprise chondrocytes.

In some embodiments, the present disclosure provides cell banks comprising cultured allogeneic human chondrocytes at a density of at least 250,000 cells per $cm^2$, wherein cultured chondrocytes are cryogenically frozen and characterized by a quality control assay.

In some embodiments, a cell bank comprises human cadaver chondrocytes. In some embodiments, a cell bank comprises primary cultures. In some embodiments, a cell bank comprises secondary cultures.

In some embodiments, a quality control assay comprises one or more of agarose, six well plate, and cell pellet assays.

In some embodiments, the present disclosure provides methods of preparing a cell bank, wherein the methods comprise steps of obtaining a tissue sample from a human, inspecting a tissue sample for contamination, weighing a tissue sample, mincing a tissue sample, digesting a tissue sample, counting cells in a tissue sample to determine viability, culturing cells; and/or, cryogenically freezing cells for storage.

In some embodiments, methods comprise a step of obtaining a tissue sample comprising removing cartilage from a human cadaver. In some embodiments, methods comprise a step of obtaining a tissue sample comprises removing cartilage from a human cadaver within about 24 hours to about 7 days after death. In some embodiments, methods comprise a step of obtaining a tissue sample comprises removing cartilage from a human cadaver within about 24 hours after death.

In some embodiments, a tissue sample is inspected for synovium, bone, fibrous tissue, fatty tissue, and/or contamination.

In some embodiments, a tissue sample weighs between about 1 g and about 9 g. In some embodiments, a tissue sample weighs about 9 g. In some embodiments, a tissue sample is divided into pieces weighing between about 200 mg and about 400 mg. In some embodiments, a tissue sample is divided into pieces weighing between about 200 mg and about 300 mg. In some embodiments, a tissue sample is divided into pieces weighing between about 280 mg and about 300 mg. In some embodiments, a tissue sample is divided into pieces weighing about 300 mg.

In some embodiments, tissue is digested with a protease. In some embodiments, tissue is digested with collagenase.

In some embodiments, a tissue sample is minced into pieces from about 0.5 $mm^2$ to about 3 $mm^2$. In some embodiments, a tissue sample is minced into pieces from about 0.5 $mm^2$ to about 2 $mm^2$. In some embodiments, a tissue sample is minced into pieces from about 0.5 $mm^2$ to about 1 $mm^2$. In some embodiments, a tissue sample is minced into pieces of about 0.5 $mm^2$.

In some embodiments, cells are counted with a hemacytometer. In some embodiments, a tissue sample comprises from about 50% to about 100% viable cells. In some embodiments, a tissue sample comprises from about 70% to about 100% viable cells. In some embodiments, a tissue sample comprises about 70% viable cells.

In some embodiments, cells are cultured in medium comprising DMEM. In some embodiments, a sample is cultured in medium comprising DMEM, HEPES, Fetal Bovine Serum, and Gentamicin. In some embodiments, cells are cultured at about 37° C.

In some embodiments, cells are cryogenically frozen at about −80° C. for about 2 to 24 hours. In some embodiments, cells are cryogenically frozen and stored in liquid nitrogen.

In some embodiments, the present disclosure provides methods of characterizing a cell bank sample. In some embodiments, the methods comprise a step of thawing cryogenically frozen primary cell bank samples, culturing secondary samples from primary samples, culturing tertiary samples from secondary samples; and/or assaying samples to determine cell viability, mycoplasma, endotoxin, sterility, senescence, identity, and aggrecan values.

In some embodiments, samples are assayed using an agarose assay. In some embodiments, an agarose assay tests for percentage of cells forming colonies for greater than or equal to two divisions. In some embodiments, an acceptance criterion of the agarose assay comprises at least 6.8% of cells form colonies for at least two divisions.

In some embodiments, samples are assayed using a six well plate assay. In some embodiments, a six well plate assay tests for an average number of cells per well. In some embodiments, an acceptance criterion of the six well assay comprises an average of cells per well that is greater than or equal to $0.88 \times 10^5$.

In some embodiments, samples are assayed using a pellet culture assay. In some embodiments, a pellet culture assay tests for ability of cells to generate cartilage following cellular culture expansion. In some embodiments, an acceptance criterion of the pellet culture assay comprises dga greater than or equal to −4.73 Ct.

In some embodiments, an acceptance criterion for the assay for mycoplasma comprises no detectable level.

In some embodiments, an acceptance criterion for the assay for sterility comprises no detection of growth.

In some embodiments, an acceptance criterion for cell viability comprises at least 70% viable cells.

In some embodiments, an acceptance criterion for senescence comprises cultures do not senesce in less than 5 passages or cultures are not immortal.

In some embodiments, an acceptance criterion for identity comprises identification of the presence of chondrocytes.

In some embodiments, the present disclosure provides methods of culturing a cell bank sample. In some embodiments, the methods comprise a step of thawing a cryogenically frozen cell bank sample, adding culture medium to a flask, counting cells to determine viability, growing cells in a cell culture medium, feeding a cell culture, and/or treating a cell culture with trypsin.

In some embodiments, a cryogenically frozen cell bank sample is thawed in a water bath, a heat block, or a dry cell bath at about 37° C.

In some embodiments, a sample is cultured in medium comprising DMEM.

In some embodiments, cells are counted with a hemacytometer.

In some embodiments, a cell culture is fed at least every 1 to 4 days.

In some embodiments, a cell culture is treated with 0.05% trypsin solution. In some embodiments, a cell culture is treated with trypsin solution until cells are detached from the flask.

BRIEF DESCRIPTION OF THE DRAWING

The present teachings described herein will be more fully understood from the following description of various illustrative embodiments, when read together with the accompanying drawing. It should be understood that the drawing described below is for illustration purposes only and is not intended to limit the scope of the present teachings in any way.

DEFINITIONS

Figure 1:
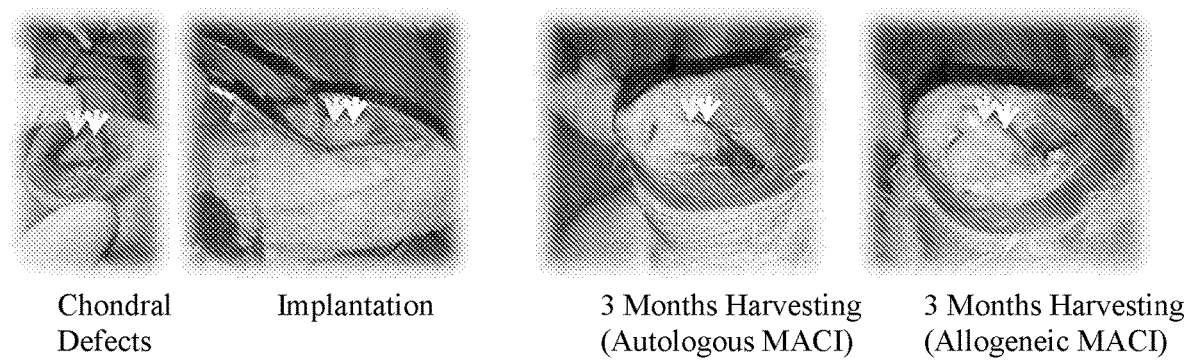
FIG. 1 depicts an exemplary series of photographs showing cartilage regeneration using both autologous and allogeneic chondrocytes.
Figure 2:
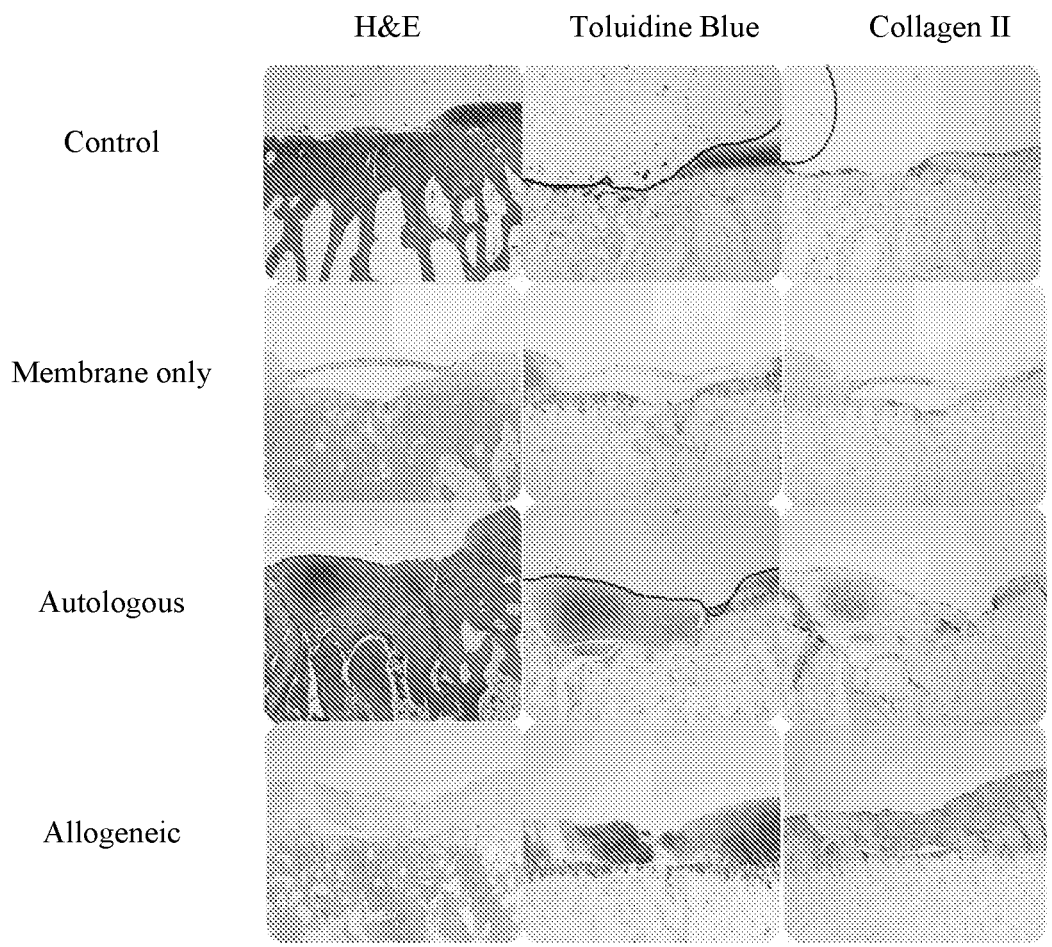
FIG. 2 depicts an exemplary series of histological samples showing cartilage regeneration using both autologous and allogeneic chondrocytes.

As used herein, the term "about," as used in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

As used herein, the term "adult" refers to a human seventeen years of age or older. In some embodiments, a human adult has a weight within the range of about 90 pounds to about 250 pounds.

As used herein, the term, "associated with" refers to two events or entities when presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to a disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

As used herein, the term "biocompatible" refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

As used herein, the term "chondrocytes" or "cartilage cells," refers to cells that are capable of expressing biochemical markers characteristic of chondrocytes, including but not limited to type II collagen, aggrecan, chondroitin sulfate and/or keratin sulfate. In some embodiments, chondrocytes, or cartilage cells, express morphologic markers characteristic of smooth muscle cells, including but not limited to a rounded morphology in vitro. In some embodiments, chondrocytes, or cartilage cells, are able to secrete type II collagen in vitro. In some embodiments, chondrocytes, or cartilage cells, are able to secrete aggrecan in vitro.

In some embodiments, chondrocytes, or cartilage calls, are able to generate tissue or matrices with hemodynamic properties of cartilage in vitro.

As used herein, the term "density" refers to an average number of a substance, for example, cells or another object, per unit area of volume. In some embodiments, density is cell density, i.e., number of cells per unit of surface area. In some embodiments, an average density is approximated by dividing a number of cells seeded by a macroscopic surface are of a surface on which they are grown. In some embodiments, a surface is two-dimensional. In some embodiments, a surface is three-dimensional.

As used herein, the term "inoculating" refers to a process or step whereby cells are brought into contact with a surface, for example a surface of a container suitable for cell culture. In some embodiments, cells inoculated onto a cell culture surface (e.g., flask, dish) adhere for a period of time. In some embodiments, once inoculated onto a cell culture surface, cells proliferate. In some embodiments, cells (e.g., chondrocytes) inoculated onto a cell culture surface may de-differentiate. In some embodiments, cells (e.g., chondrocyte precursors, mesenchymal stem cells) inoculated onto a cell culture surface may differentiate into a desired cell type, e.g., chondrocytes.

As used herein the term "in vitro" refers to events that occur in an artificial environment, e.g., in a test tube or reaction vessel, in cell culture, etc., rather than within a multi-cellular organism.

As used herein the term "in vivo" refers to events that occur within a multi-cellular organism, such as a human and a non-human animal. In the context of cell-based systems, the term may be used to refer to events that occur within a living cell (as opposed to, for example, in vitro systems).

As used herein, the term "medium" refers to components which support growth or maintenance of cells in culture. In some embodiments, this may include traditional liquid cell culture medium and an additional factor. In some embodiments, additional factors may include, for example, serum, antibiotics, growth factors, pharmacological agents, buffers, pH indicators and the like. In some embodiments, medium may be used in a process to isolate cells (e.g., chondrocytes and/or chondrocyte precursors) from a tissue sample (e.g., a cartilage sample). In some embodiments, tissue is mechanically disrupted (e.g., chopped, minced, blended) then combined with medium. In some embodiments, medium comprises enzymes (e.g., collagenase, protease) to digest tissue and release cells.

As used herein, the term "conditioned medium" refers to medium which has been contacted with cells to allow for the composition of medium to be modified, for example by uptake or release of one or more metabolites, nutrients, or factors.

As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the patient is receiving or has received certain therapy to diagnose and/or to treat a disease, disorder, or condition.

As used herein, the term "seeding" refers to a process or step whereby cells are brought into contact with a support matrix, and adhere (with or without an adhesive) to a support matrix (e.g., a collagen membrane) for a period of time. Seeded cells may divide and/or differentiate on a support matrix. In some embodiments, cells are seeded onto a support matrix prior to being implanted into a subject.

As used herein, the term "subject" refers to an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered. In some embodiments, a subject is a donor of a biological sample, tissue and/or material.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

As used herein, the term "substantially free of endotoxin" refers to a level of endotoxin per dose of a composition that is less than is allowed by the FDA for a biologic product (i.e., total endotoxin of 5 EU/kg body weight per hour, which for an average 70 kg person is 350 EU per total dose).

As used herein, the term "substantially free of mycoplasma and/or microbial contamination" refers to a negative reading for a generally accepted test of contamination known to those skilled in the art. For example, mycoplasma contamination is determined by subculturing a product sample in broth medium and distributing the culture over agar plates on days 1, 3, 7, and 14 at 37° C. with appropriate positive and negative controls. In some embodiments, mycoplasma contamination is determined using a real-time PCR method. The product sample appearance is compared microscopically at 100×, to that of a positive and negative control. Additionally, presence of mycoplasma contamination may be detected by inoculation of an indicator cell culture, which is incubated for 3 and 5 days then examined at 600× by epifluorescence microscopy using a DNA-binding fluorochrome. The composition is considered satisfactory if agar and/or broth media procedure and indicator cell culture procedure show no evidence of mycoplasma contamination. In some embodiments, an assay that may be utilized to assess a level of microbial contamination may be or comprise the U.S. Pharmacopeia (USP) Direct Transfer Method. This involves inoculating a sample into a tube containing tryptic soy broth media and fluid thioglycollate media. Tubes are observed periodically for a cloudy appearance (turbidity) during a specified period (e.g., 14 days) of incubation. A cloudy appearance on any day in either medium indicates contamination, with a clear appearance (no growth) indicating that a composition may be considered to be substantially free of contamination. In some embodiments, an approved alternative to a USP method for detection of microbial contamination is used, for example, a BacT/ALERT test using different media formulations.

As used herein, the term "surface area" refers to, for example, square area, $cm^2$, or to the macroscopic surface area of a substrate.

As used herein, the term "treatment" (also "treat" or "treating") refers to administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION OF CERTAIN EMBODIMENTS

The present disclosure provides certain compositions comprising chondrocytes, particularly of human origin, and various related methods (e.g., methods of use and/or of manufacture) of such compositions and/or associated technologies. In particular, the present disclosure provides compositions comprising allogeneic human chondrocytes which compositions may be useful, for example, for treatment of chondral and/or osteochondral lesions (e.g., for example, focal lesions in the load bearing region of a knee's articular cartilage). That is, the present disclosure provides compositions comprising human chondrocytes from a first human subject for use in treating damage in a second human subject, different from the first human subject.

In some embodiments, in accordance with the present disclosure, human chondrocytes harvested from a first human subject are cultured ex vivo (e.g., in vitro), and are seeded onto a resorbable support matrix (e.g., a collagen membrane), that may be implanted into a second human subject.

Among other things, the present disclosure provides technologies for producing cultured preparations (e.g., suspensions) of allogeneic human chondrocytes, including preparations that display certain characteristics (e.g., cell yield, cell suspension density, viability, sterility etc.), and/or technologies for preparing, storing, transporting and/or utilizing such cultured preparations.

In some embodiments, the present disclosure provides technologies for producing compositions in which cultured allogeneic human chondrocyte cells are seeded onto a resorbable support matrix according to certain parameters (e.g., membrane integrity, cell viability, cell identity, sterility), and/or technologies for preparing (e.g., performing seeding), storing, transporting and/or utilizing such compositions.

In some embodiments, the present disclosure provides technologies that permit and/or achieve treatment of clinically significant chondral and/or osteochondral lesions, defects, injuries and/or trauma. In some embodiments, treatment comprises tissue repair and/or regeneration.

In some embodiments, compositions comprising chondrocytes are implanted into a subject at or near a site of a lesion, defect, injury and/or trauma, for example, at or near an articular surface. Articular surfaces that may be treated using the compositions of the present disclosure include articular surfaces of, for example, a knee, ankle, wrist, hip, elbow or shoulder.

In some embodiments, the present disclosure provides compositions, methods, and uses of a cell bank. In some embodiments, a cell bank is created from human chondrocytes harvested from a first human subject that are cultured ex vivo (e.g., in vitro), and cryogenically frozen.

Compositions

Compositions of the present disclosure comprise human chondrocytes expanded in culture and seeded onto a support matrix.

Cell Preparations

The present disclosure utilizes allogeneic human chondrocytes for preparation of useful compositions as described herein. Typically, allogeneic human chondrocytes are isolated from tissue of a first subject, who is a different subject from that into whom provided compositions will be implanted.

In some embodiments, allogeneic human chondrocytes are obtained from tissue harvested from a human. In some embodiments, allogeneic human chondrocytes are obtained from tissue harvested from an adult human. Alternatively or additionally, in some embodiments, allogeneic human chondrocytes are obtained from tissue harvested from a cadaver. In some embodiments, allogeneic human chondrocytes are obtained from a cell bank.

Harvested tissue is typically subjected to one or more processing steps so that a source cell preparation comprising chondrocytes and chondrocyte precursors may be isolated.

Such a source cell preparation is utilized to prepare a cultured allogeneic human chondrocyte preparation for use in accordance with the present disclosure. Those skilled in the art are aware that human chondrocyte cells typically express certain detectable markers such as, for example, HAPLN1. See, for example, U.S. Pat. No. 8,029,992, which describes certain markers expressed on cultured human chondrocyte cells and whose teachings in that regard are incorporated herein by reference.

In some embodiments, a preparation of human chondrocytes useful in accordance with the present disclosure is characterized by expression levels of one or more relevant markers by cells within a preparation. For example, in some embodiments, one or more chondrocyte markers are present at a level above a particular threshold in a preparation. Alternatively or additionally, in some embodiments, one or more markers of a non-chondrocyte cell type (e.g., one or more fibroblast and/or synoviocyte markers) are present at a level below a particular threshold in a preparation (e.g., MFAP5). Those skilled in the art will be familiar with techniques for determining marker level (e.g., detection of RNA and/or protein according to known technologies).

In some embodiments, RNA expression levels for genes overexpressed by chondrocytes (e.g., HAPLN1) are measured in cultured cells. In some embodiments, RNA expression for genes overexpressed by synoviocytes (e.g., MFAP5) is measured in cultured cells. In some embodiments, RNA expression levels are presented as a ratio of expression of a chondrocyte marker (e.g., HAPLN1) versus expression of a synoviocyte marker (MFAP5). In some embodiments, cultured chondrocytes demonstrate relative RNA expression levels (HAPLN1 vs. MFAP5) of about −2, about −1, about 0, about +1, about +2, about +3, about +4, about +5, about +6, about +7, about +8 about +9, about +10 or more on a log scale. In some embodiments, cultured chondrocytes demonstrate relative RNA expression levels ranging from about −2 to about +10, about −1 to about +9, about 1 to about 10, about +3 to about +8, about +5 to about +7 or ranges therein. In some embodiments, cultured synoviocytes demonstrate relative RNA expression levels of about less than −2 on a log scale. In some embodiments, cultured synoviocytes demonstrate relative RNA expression levels ranging from less than −2 to −10 on a log scale.

In some embodiments, chondrocytes prepared from a source cell preparation are present in culture at a density sufficient to seed a support matrix with at least 250,000 cells/cm$^2$. In some embodiments, chondrocytes expanded in culture are dedifferentiated when present in a monolayer culture. In some embodiments, dedifferentiated chondrocytes exhibit a fibroblastic phenotype. In some embodiments, dedifferentiated chondrocytes down regulate expression of a gene encoding ECM, for example, ACAN and/or COL2A1. In some embodiments, dedifferentiated chondrocytes produce and/or secrete a lesser amount of ECM, for example, collagen (e.g., type II collagen) and/or aggrecan (also known as cartilage-specific proteoglycan core protein or chondroitin sulfate proteoglycan 1). Without wishing to be bound by theory, de-differentiation occurs after removal of chondrocytes from 3-dimensional cartilage matrix and is observed during expansion of cells in monolayer culture.

In some embodiments, chondrocyte preparations disclosed herein comprise a sufficient number of cells to seed a support matrix. In some embodiments, chondrocyte preparations comprise at least about $3\times10^6$, $4\times10^6$, $5\times10^6$, $6\times10^6$, $7\times10^6$, $8\times10^6$, $9\times10^6$ or more cells following a second passage. In some embodiments, chondrocyte preparations comprise at least about $3\times10^6$ cells after a second passage. In some embodiments, chondrocyte preparations disclosed herein comprise at least about $1\times10^7$, $2\times10^7$, $3\times10^7$, $4\times10^7$, $5\times10^7$, $6\times10^7$, $7\times10^7$, $8\times10^7$, $9\times10^7$ or more cells at a final passage. In some embodiments, chondrocyte preparations disclosed herein comprise at least $1\times10^7$ cells at a final passage.

In some embodiments, chondrocyte cultures are about 50%, 60%, 70%, 80%, 90%, 95%, 98% or more confluent. In some embodiments, chondrocyte cultures are about 100% confluent. In some embodiments, chondrocyte cultures are about 50% to 90% confluent.

In some embodiments, chondrocytes are seeded on a support matrix at density of at least 250,000 cells/cm$^2$, 300,000 cells/cm$^2$, 400,000 cells/cm$^2$, 500,000 cells/cm$^2$, 600,000 cells/cm$^2$, 700,000 cells/cm$^2$, 800,000 cells/cm$^2$, 900,000 cells/cm$^2$, 1,000,000 cells/cm$^2$, or more.

Among other things, the present disclosure provides cell preparations in which a significant percentage of cells are viable; such high viability cell preparations can materially improve, and may be required for, successful treatment of a particular lesion or defect. In some embodiments, at least 70%, 75%, 80%, 85%, 90%, 95%, 98% or more of cells present in a preparation are viable. In some embodiments, at least 90% of chondrocytes in a preparation are viable.

In some embodiments, a composition of the disclosure provided herein is substantially free of components used during preparation of a source cell preparation and during expansion of chondrocytes (e.g., fetal bovine serum albumin, fetal bovine serum and/or horse serum). For example, in some embodiments, a composition provided herein comprises less than 10 µg/ml, 5 µg/ml, 4 µg/ml, 3 µg/ml, 2 µg/ml, 1 μg/ml, 0.05 μg/ml fetal bovine serum albumin. In some embodiments, a cell preparation is substantially free of mycoplasma, endotoxin, and/or microbial (e.g., aerobic microbe(s), anaerobic microbes(s) and/or fungi) contamination. In some embodiments, a cell preparation tests negative for mycoplasma, endotoxin and/or microbial contamination.

Support Matrix

A support matrix for use in accordance with the present disclosure is made of a material to which human allogeneic chondrocyte cells adhere. In some embodiments, a support matrix comprises and/or is coated with an adhesive agent that facilitates and/or enables cell adherence.

In some embodiments, a support matrix supports cell proliferation.

In some embodiments, a support matrix is bioresorbable. In some such embodiments, a bioresorbable matrix may degrade over a period of hours, days, weeks or months. For example, a bioresorbable matrix may degrade within at least 24 hours, at least 7 days, at least 30 days or at least 6 months. In some embodiments, a support matrix may act as a hemostatic barrier inhibiting penetration of adjacent cells and tissues into a particular area of the body, for example, an area requiring treatment (e.g., an articular joint).

In some embodiments, a support matrix is a gel, a solid, or a semi-solid. In some embodiments, a support matrix is impermeable, permeable or semi-permeable (e.g., comprising pores). In some embodiments, a support matrix is comprised of a synthetic material, a natural material, or a combination thereof.

In some embodiments, a support matrix may have a structure that comprises a membrane, microbead, fleece, thread, gel or combination thereof.

In some embodiments, a support matrix may be or comprise biological material generated by cells; in some such embodiments, a biological material is generated by cells in culture. Alternatively, in some such embodiments, a biological material is generated by cells in tissue (e.g., in vivo). In some embodiments, such biological material is generated by cells that are allogeneic to a subject who will receive treatment as described herein.

In some embodiments, a support matrix may be or comprise collagen. For example, a support matrix may be or comprise type I collagen, type II collagen, type III collagen, or a combination thereof (e.g., may include a combination of type I collagen and type II collagen, or may include a combination of type I collagen and type III collagen). In some embodiments, a support matrix is comprised of primarily type I collagen on a first side and type III collagen on a second side. In some embodiments, a first side of a support matrix comprising type I collagen is a smooth surface. In some embodiments, a second side of a support matrix comprising type III collagen is a rough surface. In some embodiments, a rough surface of a support matrix is suitable for cell seeding. In some embodiments, a smooth surface of a support matrix is suitable to contact a joint surface.

In some embodiments, some or all collagen in a support matrix for use in accordance with the present disclosure may be cross-linked; in some embodiments, it may be uncross-linked.

In some embodiments, collagen utilized in accordance with the present disclosure is derived from an animal such as a pig. In some embodiments, collagen is derived from the peritoneum of a pig.

In some embodiments as described herein, a support matrix comprises a combination of type I and type III porcine collagen.

In some embodiments, cells (e.g., chondrocytes) seeded onto and/or cultured on a support matrix as described herein may produce one or more extracellular matrix proteins (e.g., collagen) that interact with and/or become incorporated into, a support matrix In some embodiments, a support matrix may also include proteins, polypeptides, hyaluronic acid) and/or polymers (e.g., elastin, fibrin, laminin, fibronectin). In some embodiments, a support matrix is cell-free.

In some embodiments, a support matrix has a surface area, size, shape, and/or dimension appropriate for treatment of a particular chondral or osteochondral defect, lesion or injury. In some embodiments, a support matrix is provided in a form (e.g., a sheet form) that is readily shaped (e.g., by folding, cutting, trimming etc.) for administration to a particular chondral or osteochondral defect.

In some embodiments, a surface area of a support matrix is at least about 5 cm$^2$, 10 cm$^2$, 12 cm$^2$, 13 cm$^2$, 13.5 cm$^2$, 14 cm$^2$, 14.5 cm$^2$, 15 cm$^2$, 15.5 cm$^2$, 16 cm$^2$, 17 cm$^2$, 18 cm$^2$, 19.5 cm$^2$, 20 cm$^2$, 20.5 cm$^2$, 21.5 cm$^2$, 22 cm$^2$, 25 cm$^2$, 30 cm$^2$ or larger. A dimension of a support matrix may be any dimension necessary to achieve a desired surface area suitable for treating a chondral and/or osteochondral defect. For example, dimensions of a 20 cm$^2$ support matrix may be about 2 cm×10 cm, 2.5 cm×8 cm, 3 cm×6.7 cm or 4 cm×5 cm. In some embodiments, a surface area of a support matrix (e.g., collagen membrane) may be about 14.5 cm$^2$ with dimensions of about 3 cm×5 cm. In some embodiments, a surface area of a support matrix (e.g., collagen membrane) may be about 20 cm$^2$ with dimensions of about 4×5 cm$^2$.

Cell Seeded Support Matrix

Among other things, the present disclosure provides compositions comprising cultured human chondrocytes seeded onto a support matrix (e.g., collagen membrane).

Typically, cells that have been cultured for a period of time (e.g., 3 days to 5 weeks) are present on or in a support matrix. In some embodiments, cells seeded onto a support matrix are adherent. In some embodiments, cells are adherent to a support matrix to an extent that they do not wash off a matrix during subsequent cell culturing steps, are not displaced from a matrix during transported and/or not displaced from a matrix during a surgical procedure to implant a matrix.

Among other things, the present disclosure provides cell seeded support matrices in which a significant percentage of cells are viable; such high viability of cells present on a cell seeded matrix can materially improve, and may be required for, successful treatment of a particular lesion or defect. In some embodiments, at least 70%, 75%, 80%, 85%, 90%, 95%, 98% or more of cells present on a cell seeded matrix are viable. In some embodiments, at least 90% of chondrocytes present on a cell seed matrix are viable.

Cells seeded onto a cell seeded support matrix are viable for at least about 1 day, 2 days, 3 days, 4, days, 5 days, 6 days, 7 days, 8 days, 9 days, 10 days, 11 days, 12 days, 13 days, 2 weeks, 3 weeks or more. In some embodiments, cells seeded onto a support matrix divide. In some embodiments, a cell seeded support matrix is stored at about 4° C. to about 37° C.

In some embodiments, a cell seeded support matrix comprises at least 250,000 cells/cm$^2$, 300,000 cells/cm$^2$, 400,000 cells/cm$^2$, 500,000 cells/cm$^2$, 600,000 cells/cm$^2$, 700,000 cells/cm$^2$, 800,000 cells/cm$^2$, 900,000 cells/cm$^2$, 1,000,000 cells/cm$^2$, or more. In some embodiments, a cell seeded matrix comprising greater than 250,000 cells/cm$^2$ 300,000 cells/cm$^2$, 400,000 cells/cm$^2$, 500,000 cells/cm$^2$, 600,000 cells/cm$^2$, 700,000 cells/cm$^2$, 800,000 cells/cm$^2$, 900,000 cells/cm$^2$, 1,000,000 cells/cm$^2$ is suitable for implant into a subject.

In some embodiments, a cell seeded support matrix comprises at least $5\times10^6$, $7.5\times10^6$, $1.0\times10^7$, $1.5\times10^7$, $2.0\times10^7$, $2.5\times10^7$, $3.0\times10^7$ or more cells. In some embodiments, a 20 cm$^2$ porcine type I and type III collagen membrane comprises about $1.0\times10^7$ chondrocytes to about $2.0\times10^7$ chondrocytes. In some embodiments, a 14.5 cm$^2$ porcine type I and type III collagen membrane comprises about $7.5\times10^6$ chondrocytes to about $1.5\times10^7$ chondrocytes.

In some embodiments, a cell seeded support matrix may also comprise medium (e.g., DMEM) and supplements (e.g., fetal bovine serum, antibiotic). In some embodiments, medium comprises about 7%, about 8%, about 9%, about 10%, about 11% fetal bovine serum. In some embodiments, medium is supplemented with 8.9%+/−0.2% fetal bovine serum and gentamicin.

In some embodiments, a cell seeded support matrix has a surface area of at least about 5 cm$^2$, 10 cm$^2$, 12 cm$^2$, 13 cm$^2$, 13.5 cm$^2$, 14 cm$^2$, 14.5 cm$^2$, 15 cm$^2$, 15.5 cm$^2$, 16 cm$^2$, 17 cm$^2$, 18 cm$^2$, 19.5 cm$^2$, 20 cm$^2$, 20.5 cm$^2$, 21.5 cm$^2$, 22 cm$^2$, 25 cm$^2$, 30 cm$^2$. In some embodiments, a cell seeded support matrix has a surface area of about 20 cm$^2$ (e.g., 4 cm×5 cm). In some embodiments, a cell seeded support matrix has a surface area of about 14.5 cm$^2$ (e.g., about 3 cm×5 cm). In some embodiments, a cell seeded support matrix is trimmed, shaped, cut, molded or formed and corresponds to a shape of a defect, lesion and/or injury in need of treatment. In some embodiments, a cell seeded support matrix is of an irregular shape.

In some embodiments, a cell seeded support matrix is substantially free of components used during preparation of a source cell preparation of during expansion of chondrocytes (e.g., fetal bovine serum albumin, fetal bovine serum and/or horse serum). For example, in some embodiments, a cell seeded support matrix provided herein comprises less than 10 μg/ml, 5 μg/ml, 4 μg/ml, 3 μg/ml, 2 μg/ml, 1 μg/ml, 0.05 μg/ml fetal bovine serum albumin. In some embodiments, a cell seeded support matrix is substantially free of mycoplasma, endotoxin, and/or microbial (e.g., aerobic microbe(s), anaerobic microbes(s) and/or fungi) contamination.

In some embodiments, a cell seeded support matrix composition, prepared in accordance with the present disclosure, comprises a biocompatible adhesive or glue. In some embodiments, a least a portion of a cell is coated with a biocompatible adhesive or glue. In some embodiments, a biocompatible adhesive or glue forms a layer over cells on a support matrix. In some embodiments, a biocompatible adhesive or glue forms a layer under cells on a support matrix. In some embodiments, a cell seeded support matrix comprises multiple layers of biocompatible adhesive or glue and cells. In some embodiments, a biocompatible adhesive or glue is impregnated within a support matrix.

In some embodiments, the present disclosure provides for cells and glue, and/or adhesive, combined together in a mixture of one or more alternating layers of cells and glue, and/or adhesive, on a surface or edge of a support matrix.

In some embodiments, biocompatible adhesives or glues used in compositions of the disclosure include an organic fibrin glue (e.g., TISSEEL®, fibrin based adhesive available from Baxter, Austria) or a fibrin glue prepared during surgery using autologous blood.

Methods of Preparation

In some embodiments, allogeneic human chondrocytes are obtained from tissue harvested from a human. In some embodiments, allogeneic human chondrocytes are obtained from tissue harvested from an adult human. In some embodiments, a source tissue sample may be obtained from a human subject who is living. Alternatively or additionally, in some embodiments, allogeneic human chondrocytes are obtained from tissue harvested from a cadaver. When a sample is obtained from a human cadaver, a sample may be collected within 24 hours of death or alternatively, up to 1 week after death.

In some embodiments, cells of the composition may be obtained from a human subject by biopsy, resection, excision and/or dissection of a source tissue sample comprising chondrocytes or chondrocyte precursors. In some embodiments, bone is included in a tissue sample because it increases likelihood or number of viable cells. In some embodiments, a human subject is an adult. In some embodiments, an adult is about 18 to 30 years of age, 18 to 40 years of age, 18 to 50 years of age, 18 to 55 years of age or 18 to 60 years of age. In some embodiments, a sample is obtained from an adult about 20 to 30 years of age. In some embodiments, a human subject is a juvenile. In some embodiments, a human subject is about 1 to 17 years of age. In some embodiments a human subject is about 12 to 39 years of age. In some embodiments a human subject is at least 10 years of age. The present disclosure contemplates that a source tissue sample comprising chondrocytes, or chondrocyte precursors, is obtained from a human subject other than a subject(s) in need of treatment (e.g., cells are allogeneic).

In some embodiments, a tissue sample is subject to inspection to ensure physical integrity. In some embodiments, the inspection is visual. In some embodiments, a tissue sample is inspected to determine the media type it is transported in. In some embodiments, a tissue sample is inspected to determine if the tissue was received in frozen media. In some embodiments, a tissue sample is inspected to determine if foreign matter is present. In some embodiments, a tissue sample is inspected to determine if the transport media is expired. In some embodiments, damaged cartilage is segregated. In some embodiments, abnormal cartilage is segregated. In some embodiments, damaged cartilage is rejected. In some embodiments, abnormal cartilage is rejected.

In some embodiments, a tissue sample is inspected for synovium. In some embodiments, a tissue sample is inspected for bone. In some embodiments, a tissue sample is inspected for unwanted tissue. In some embodiments, a tissue sample is inspected for areas with a lack of rigidity. In some embodiments, a tissue sample is inspected by prodding each side to detect one or more areas that lack rigidity. In some embodiments a tissue sample is inspected for membranous tissue. In some embodiments, a tissue sample is inspected for fibrous tissue. In some embodiments, a tissue sample is inspected for fatty tissue. In some embodiments, presence of one or more of bone, synovium, thin tissue, buoyant tissue, or unusual color can indicate that a tissue sample may yield fewer chondrocytes after tissue processing.

In some embodiments, a source cell preparation is prepared from a tissue sample within about 6 hours, 12 hours, 24 hours, 2 days, 3 days, 4 days, 5 days, 6 days, 1 week, 2 weeks, 3 weeks or 4 weeks following collection of a tissue sample from a human subject. In some embodiments, a tissue sample is subject to processing. In some embodiments, chondrocytes are isolated from a tissue sample. In some embodiments, a tissue sample is transported in transport media. In some embodiments, a tissue sample is capable of being stored in transport media for up to seven days following procurement. In some embodiments, transport media is decanted away from a tissue sample. In some embodiments, transport media is aspirated away from a tissue sample.

In some embodiments, once a tissue sample is isolated, any bone and synovium, if present, are trimmed away. In some embodiments, after trimming, the target final weight of a tissue sample is less than or equal to 9 g. In some embodiments, trimmed a tissue sample weighing between about 1 g and about 9 g is processed. In some embodiments, trimmed a tissue sample weighing about 9 g is processed. In some embodiments, trimmed a tissue sample weighing less than 1 g is not processed. In some embodiments, trimmed a tissue sample weighing more than 9 g is not processed. In some embodiments, trimmed a tissue sample is divided into approximately 300 mg samples. In some embodiments, a tissue sample is divided into samples weighing between about 200 mg and about 400 mg. In some embodiments a tissue sample is divided into samples weighing between about 250 mg and about 320 mg. In some embodiments, a tissue sample is divided into samples weighing between about 280 mg and about 300 mg. In some embodiments, a tissue sample weighs about 300 mg. In some embodiments a tissue sample does not weigh less than about 280 mg. In some embodiments, each tissue sample is processed separately.

In some embodiments, a tissue sample is subjected to mechanical disruption to release cells. In some embodiments, prior to enzymatic treatment, tissue is minced to aid in digestion. In some embodiments, tissue is minced into pieces of about 2 mm$^2$ to about 3 mm$^2$. In some embodiments, tissue is minced into pieces of about 1 mm$^2$ to about 2 mm$^2$. In some embodiments, tissue is minced into pieces of about 0.5 mm$^2$ to about 1 mm$^2$. In some embodiments, tissue is minced into pieces of about 0.5 mm$^2$.

In some embodiments a tissue sample is subjected to enzymatic treatment. In some embodiments, a tissue sample is be washed and incubated in a cell growth medium containing an enzyme(s) to digest tissue surrounding the cells without damaging the cells. In some embodiments, tissue is digested using a combination of a non-specific protease and collagenase. In some embodiments, tissue comprising chondrocytes may be digested using cell growth medium comprising a non-specific protease. In some embodiments, tissue is digested for about 30 minutes to about 90 minutes, about 30 minutes to about 2 hours, about 60 minutes to about 90 minutes or about 60 minutes to about 2 hours at 37° C. In some embodiments, a cartilage sample is digested in non-specific protease for 60-90 minutes. Following treatment with a non-specific protease, in some embodiments, tissue is further digested with collagenase in cell growth medium. In some embodiments, tissue is digested for about 8 hours to about 16 hours, about 8 hours to about 24 hours, about 8 hours to about 32 hours, about 16 hours to about 24 hours or about 16 hours to about 32 hours at 37° C. In some embodiments, a cartilage sample is digested in collagenase for about 16 to 24 hours. In some embodiments, tissue is digested in a 5% $CO_2$ atmosphere. In some embodiments, tissue is digested in a closed container. In some embodiments, cell growth medium includes Dulbecco's Modified Eagle Medium (DMEM), about 20% (+/−1%) irradiated fetal bovine serum (irFBS), and optionally an antibiotic (e.g., 40 µg/mL gentamicin), an antifungal, and factor(s) for induction of lineage cell differentiation (hereinafter "cell growth medium"). In some embodiments, cell growth medium includes ascorbic acid and or transforming growth factor-β (TGF-β). In some embodiments, cell growth medium includes HEPES. In some embodiments, cell growth medium includes glutamax. In some embodiments, cell growth medium includes high glucose. In some embodiments, cell growth medium includes L-glutamine. In some embodiments, cell growth medium comprises DMEM, HEPES, Fetal Bovine Serum, and Gentamicin In some embodiments, following steps of digestion, cells are isolated by centrifugation. In some embodiments, supernatant is decanted away from the cell pellet. In some embodiments, supernatant is aspirated away from the cell pellet. In some embodiments, centrifugation is followed by washing with cells with growth medium. In some embodiments, the cell pellet is re-suspended in growth medium.

In some embodiments, isolated cells are counted and assessed for viability. In some embodiments, cells are counted with a hemacytometer. In some embodiments, viable cells are counted. In some embodiments, non-viable cells are counted. In some embodiments viable cells per mL are calculated.

In some embodiments, following isolation, cells are cultured in cell growth medium for about 3 days to about six weeks, at 37° C. in a 5% $CO_2$ atmosphere. The culture period may vary depending upon the number of cells initially obtained. Culturing time may vary with different cell types since different cell types have different rates of proliferation.

In some embodiments, medium that supports proliferation and/or differentiation of cells in tissue culture is utilized. One of ordinary skill in that art will be aware of a variety of potentially useful media including for example, Dulbecco's Modified Eagle's Medium (DMEM), α-modified Minimal Essential Medium (α-MEM), and Roswell Park Memorial Institute Media 1640 (RPMI Media 1640) and the like. In some embodiments, up to about 20% Fetal Bovine Serum (FBS) or 1% to 20% horse serum is added to medium to support proliferation of chondrocytes.

In some embodiments, a defined medium may be used; in some such embodiments, one or more growth factors, cytokines, hormones and FBS is provided at appropriate concentrations to permit and/or facilitate cell growth, proliferation, and/or differentiation.

In some embodiments, cells are grown and/or maintained at temperatures between 31° C. and 37° C. with a $CO_2$ content between 2% and 10% and an oxygen content between 1% and 22%. In some embodiments, cells may be maintained under these conditions for up to 6 weeks.

In some embodiments, cells are maintained in culture for up to 2 passages, 3 passages, 4 passages, 5 passages, 6 passages, 7 passages, 8 passages, 9 passages, 10 passages or more.

In some embodiments, chondrocytes de-differentiate in monolayer cell culture, exhibiting a fibroblastic phenotype and down regulation of Col2 and Aggrecan. Without wishing to be bound by theory, de-differentiation occurs after removal of chondrocytes from a 3-dimensional cartilage matrix and is observed during proliferation and expansion of cells in monolayer culture.

In some embodiments, cells are cultured to a density sufficient to achieve a cell seeding density as described herein.

In some embodiments, cells are contacted with an enzyme (e.g., trypsin) for a period of time sufficient to release cells from a tissue culture surface. In some embodiments, released cells are provided as a suspension of cells. In some embodiments, a suspension of cells is brought into contact with one or more predetermined portions of a support matrix, (e.g., with one surface, a portion of a surface), such that a substantial portion of cells, or substantially all cells, contact one or more surfaces of a support matrix. In some embodiments, cells are retained only on one surface or an edge of one surface of a support matrix. In some embodiments, upon contact with a support matrix cells adhere.

In some embodiments, a support matrix (e.g., resorbable collagen membrane) is provided in a container. In some embodiments, a support matrix is placed or positioned over a bottom surface of a container. In some embodiments, a container comprises an anchor. In some embodiments, a support matrix is placed or positioned over a bottom surface of a container and an anchor is place on top of such support matrix. One of ordinary skill will be aware that an anchor placed on top of a support matrix may contact only an outer edge (e.g., peripheral edge) of a support matrix. In some embodiments, an anchor placed on top of a support matrix defines an area or volume bounded by sidewalls of such anchor and top surface of a support matrix. In some embodiments, an area or volume bounded by sidewalls of an anchor and top surface of a support matrix confines cells (e.g., chondrocytes) within such area or volume. In some embodiments, a cell seeded support matrix is secured within a container comprising an anchor.

In some embodiments, such controlled seeding of cells on and/or near a support matrix surface may allow cells to freely migrate and/or populate a site of implant, and/or may lead to enhanced cell proliferation and/or regeneration of tissue at a site of implant.

As presently disclosed, uniform seeding is preferable. Without wishing to be bound by theory, it is believed that the number of cells seeded does not limit an amount of final tissue produced in a patient treated using a cell seeded support matrix. However optimal seeding may increase a rate of cell and or tissue generation in a patient following implant. In some embodiments, optimal seeding amounts depend on culture conditions. In some embodiments, uniform seeding is characterized by a lack of gaps or space between seeded cells.

In some embodiments, chondrocytes are seeded on a support matrix (e.g., porcine type I and III collagen) at a density of at least about 250,000 cells/cm$^2$, 300,000 cells/cm$^2$, 400,000 cells/cm$^2$, 500,000 cells/cm$^2$, 600,000 cells/cm$^2$, 700,000 cells/cm$^2$, 800,000 cells/cm$^2$, 900,000 cells/cm$^2$, 1,000,000 cells/cm$^2$, or more. In some embodiments, cells seeded on a support matrix may divide and/or differentiate.

In some embodiments, a total of at least $5\times10^6$, $7.5\times10^6$, $1.0\times10^7$, $1.5\times10^7$, $2.0\times10^7$, $2.5\times10^7$, $3.0\times10^7$ or more chondrocytes are seeded on support matrix (e.g., type I and III collagen). In some embodiments, a total of about $1.0\times10^7$ chondrocytes to about $2.0\times10^7$ chondrocytes are seeded on a 20 cm$^2$ porcine type I and type III collagen membrane. In some embodiments, a total of about $7.5\times10^6$ chondrocytes to about $1.5\times10^7$ chondrocytes are seeded on a 14.5 cm$^2$ porcine type I and type III collagen membrane.

In some embodiments, a cell seeded support matrix is contacted with medium favorable to cell growth, adherence to a support matrix, viability and/or differentiation. In some embodiments, a medium comprises DMEM. In some embodiments, a medium is supplemented with substances, e.g., fetal bovine serum, antibiotic (e.g., gentamicin). In some embodiments, medium is supplemented with about 7%, about 8%, about 9%, about 10%, about 11% fetal bovine serum. In some embodiments, medium is supplemented with 8.9%+/−0.2% fetal bovine serum. In some embodiments, a membrane comprising porcine collagen type I and III seeded with allogeneic chondrocytes is contacted with DMEM supplemented with 8.9%+/−0.2% FBS and 45 µg/mL gentamicin. In some embodiments, cells seeded on a support matrix are contacted with medium as described above for at least 1, 2, 3, 4, 5, 6, 7, 8 or more days. In some embodiments, chondrocytes seeded on a support matrix are contacted with medium as described above for about 2 to 4 days.

In some embodiments, a quality assessment step is performed on a cell seeded support matrix, or a portion thereof. In some embodiments, a quality assessment step comprises evaluation or measurement of membrane integrity, presence or absence of particulate matter, cell viability, cell density, cell identity and or sterility.

In some embodiments, medium containing supplements is removed from chondrocytes seeded on a support matrix by a step comprising rinsing. In some embodiments, a rinsing step is a series of rising steps. In some embodiments, a cell seeded matrix is rinsed using medium, for example, phenol red free DMEM. In some embodiments, phenol red free DMEM is also suitable as a storage or shipping medium.

In some embodiments, a biocompatible adhesive or glue is utilized for contacting cells with a support matrix. In some embodiments, cells are mixed with a biocompatible adhesive or glue before, during and or after contact with a support matrix. In some embodiments, a biocompatible adhesive or glue may be layered over cells on a support matrix, below cells on a support matrix or impregnated within a support matrix.

In some embodiments, the present disclosure provides for combining cells and glue combined together in a mixture and forming one or more alternating layers of cells and glue on a surface or edge of a support matrix.

In some embodiments, biocompatible adhesives or glues used in compositions of the disclosure include an organic fibrin glue (e.g., TISSEEL®, fibrin based adhesive available from Baxter, Austria) or a fibrin glue prepared during surgery using autologous blood.

Methods and Uses of Cell Bank Preparation

The present disclosure contemplates storage and banking of cultured cells and/or cell seeded support matrices for later use. Also contemplated are methods of use of stored cells.

In some embodiments, a source tissue sample obtained from a single human subject provides sufficient numbers of chondrocytes, and/or chondrocyte precursors, to treat multiple other human subjects. In some embodiments, enough source tissue may be obtained from a single subject to provide sufficient chondrocytes to treat about 100, about 200, about 500, about 1000, about 1500 or about 2000 subjects.

Typically, a source tissue sample is obtained from a tissue comprising chondrocytes or chondrocyte precursors. For example, chondrocytes and chondrocyte precursors may be isolated from cartilage (e.g., hyaline cartilage, fibrocartilage or elastic cartilage) or bone marrow. In some embodiments, suitable cartilage may be located at an articular surface (e.g., knee joint) or at a meniscus. In some embodiments, suitable cartilage may be located at a femoral condyle, in particular at a superior-external region, or a lateral external region of an incisura. In some embodiments, chondrocytes isolated from a source tissue sample obtained from an articular surface are suitable for preparation of compositions described herein.

In some embodiments, a source tissue (e.g., a source cartilage) is obtained from a site in a source subject that corresponds to a lesion site in a recipient subject.

In some embodiments, cultured cells and/or cell seeded support matrices are stored at about 0° C., about 4° C., about 6° C., about 8° C., about 10° C., about 12° C., about 14° C., about 16° C., about 18° C., about 20° C., about 22° C., about 24° C., about 26° C., about 28° C., about 30° C., about 32° C., about 34° C., about 36° C., about 37° C. or higher. In some embodiments, cultured cells and/or cell seeded support matrices are stored at less than 0° C. In some embodiments, cultured cells and/or cell seeded support matrices are stored at about −5° C. to about 5° C., about 5° C. to about 10° C., about 10° C. to about 15° C., about 15° C. to about 20° C., about 20° C. to about 25° C., about 25° C. to about 30° C., about 30° C. to about 35° C., about 35° C. to about 40° C. In some embodiments, cultured cells and/or cell seeded support matrices are store at about −5° C. to about 37° C., and ranges therein. Without wishing to be bound by theory, storage advantageously enables chondrocytes to be conserved for long periods, without affecting their functional properties. In some embodiments, chondrocyte preparations and/or chondrocyte seeded collagen membranes may be stored under conditions described herein, for example, prior to in vivo implantation.

In some embodiments, a cell preparation and/or cell seeded support matrix described herein is stored for at least 24 hours, at least 2 days, at least 5 days, at least 7 days, at least 14 days, at least 21 days, at least 28 days, at least 1 month, at least 6 months, at least 12 months or longer.

In some embodiments, cells are stored as a primary cell bank (e.g., following an initial culture step). In some embodiments, cells in a primary cell are stored for at least 1, 2, 3, 4, 5, 6, 7, 8, 9 or 10 years. In some embodiments, cells are stored as a secondary, or working cell bank. A secondary, or working cell bank may be comprised of cells derived from a primary cell bank.

In some embodiments, cells are treated with trypsin prior to cryopreservation. In some embodiments, cells are treated with trypsin at a confluence level between about 50% to about 100%. In some embodiments, cells are treated with trypsin at a confluence level between about 50% to about 90%. In some embodiments, cells are treated with trypsin at a confluence level at about 70%. Alternatively, in some embodiments, cells are treated with trypsin when primary cultures have reached a maximum of 16 days of growth and when secondary cultures have reached a maximum of 10 days of growth. In some embodiments, cells are treated with 0.05% trypsin and EDTA. In some embodiments, after treatment with trypsin, cells are analyzed for viability using a hemacytometer.

In some embodiments, cells are frozen at a cell density between about $1 \times 10^6$ cells/mL. and about $5 \times 10^6$ cells/mL. In some embodiments, 20% DMSO is added to a cryopreservation vial at a volume equal to the volume of cells in the vial. In some embodiments, 20% DMSO is added to the cryopreservation vial drop-wise. In some embodiments, cells are frozen at a temperature between about −70° C. and about −60° C. In some embodiments, cells are frozen at a temperature at about −80° C. In some embodiments, cells are stored long term in liquid nitrogen vapor ($LN_2$). In some embodiments, cryopreservation vials are transferred to $LN_2$ after being frozen at about −80° C. for between about 2 hours and about 24 hours. In some embodiments, cells are stored long term for between about 1 day and about 7 years.

In some embodiments, a saline solution (e.g., a solution isotonic with plasma) is used to store chondrocytes. In some embodiments, cells or cell seeded support matrix may be stored in a solution comprising chloride salts (e.g., sodium chloride, potassium chloride, calcium chloride and/or magnesium chloride) and lactates (e.g., sodium lactate). In some embodiments, an isotonic saline solution may comprise sodium chloride, potassium chloride, magnesium chloride and sodium lactate. In some embodiments, an isotonic saline solution may comprise sodium chloride, potassium chloride, calcium chloride and sodium lactate, which is equivalent to a "Ringer-lactate solution."

In some embodiments, cells to be stored are analyzed for quality control. In some embodiments, thawed cell bank cells are analyzed for quality control. In some embodiments, primary cells are analyzed for quality control. In some embodiments, secondary cells are analyzed for quality control. In some embodiments, tertiary cells are analyzed for quality control. In some embodiments, cells are analyzed for mycoplasma. In some embodiments, cells are analyzed for endotoxins. In some embodiments, cells are analyzed for sterility. In some embodiments, cells are analyzed for viruses. In some embodiments, cells are analyzed for retroviruses. In some embodiments, cells are analyzed for karyology. In some embodiments, cells are analyzed for cell line identification (e.g. chondrocytes). In some embodiments, cells are analyzed for viability. In some embodiments, cells are analyzed for senescence. In some embodiments, cells are analyzed for confluence.

In some embodiments, cryogenically frozen cells are thawed. In some embodiments, cryogenically frozen cells are thawed for culture inoculation. In some embodiments, cells are thawed at between about 35.5° C. and about 38.5° C. In some embodiments, cells are thawed at about 37° C. In some embodiments, cells are thawed in a heat block. In some embodiments, cells are thawed in a digital dry bath unit. In some embodiments, cells are thawed in a water bath. In some embodiments thawed cells are moved to a new tube. In some embodiments the cryopreservation vial is washed with media. In some embodiments the wash is added drop-wise to the thawed cells.

In some embodiments, thawed cells are measured for viability. In some embodiments, viability is measured with a hemacytometer. In some embodiments, at least 70%, 75%, 80%, 85%, 90%, 95%, 98% or more of cells present are viable. In some embodiments, at least 90% of cells in a preparation are viable. In some embodiments at least 70% of cells in a preparation are viable.

In some embodiments percent recovery after thaw is calculated. In some embodiments the percent recovery is at least 50%, 55%, 60%, 65%, 70%, 75%, 80%, 85%, 90%, 95%, 98% or more. In some embodiments, at least 50% of cells are recovered after thaw.

Methods of Treatment

In some embodiments, the present disclosure contemplates use of chondrocytes seeded and grown on a support matrix (e.g., collagen membrane) to treat/repair cartilage defects, lesions and/or injuries in a subject. Alternatively or additionally, in some embodiments, the present disclosure contemplates use of compositions disclosed herein to regenerate cartilage in a subject. In some embodiments, cartilage defects, lesions and/or injuries are located in an articulating joint (for example, knee, ankle, elbow, shoulder, hip, or wrist) of a subject. In some embodiments, a defect in a medial femoral condyle, a lateral femoral condyle or trochlea of a subject is/are treated using compositions of the present disclosure.

In some embodiments, a subject who is treated is an adult human. In some embodiments, a subject who is treated is a human between 10 to 17 years in age; in some such embodiments, a subject does not have an open growth plate.

In some embodiments, when a cell seeded support matrix is implanted at a site of a defect, lesion and/or injury, a matrix is placed with cells facing (e.g., in contact with) a surface to be treated. In some embodiments, a cell seeded support matrix is implanted into, and/or over, a site of a lesion, defect and/or injury. In some embodiments, a cell seeded support matrix is provided in a form (e.g., a sheet form) that is readily shaped (e.g., by folding, cutting, trimming etc.) for administration to a chondral or osteochondral defect. In some embodiments, a cell seeded support matrix is shaped into a form that uniquely fits or adheres to a subject's chondral or osteochondral defect.

In some embodiments, after a cell seeded support matrix is implanted into a defect, lesion and/or injury, a covering matrix is secured using e.g., a biocompatible adhesive or suture. In some embodiments, a covering matrix serves to cover an area to prevent infiltration of undesirable cells and/or biological factors (e.g., fibroblasts, macrophages) from surrounding tissue into an area to be treated. In some embodiments, a covering matrix comprises any support matrices described herein, and/or may include hyaluronic acid, fibrin and/or polylactic acid. In some embodiments, a covering matrix is cell-free and resorbable. In some embodiments, a covering matrix is semi-permeable.

In some embodiments, biocompatible adhesives or glues used to secure a covering matrix include an organic fibrin glue or sealant (e.g., TISSEEL®, fibrin based adhesive available from Baxter, Austria) or a fibrin glue prepared during surgery using autologous blood.

In some embodiments, a biocompatible adhesive or glue is applied to a defect prior to placement of a cell seeded support matrix over, or into, a defect. In some embodiments, a biocompatible adhesive or glue is applied to a cell seeded support matrix prior to placement over, or into, a defect. In some embodiments, a biocompatible adhesive or glue is applied to a periphery of an implant.

In some embodiments, a cell seeded support matrix is injected into a site of implantation, with or without an adhesive or glue. In some embodiments, a cell seeded support matrix is implanted via a minimally invasive procedure. In some embodiments, a minimally invasive procedure consists of arthrotomy, mini-arthrotomy, arthroplasty and arthroscopy.

In some embodiments, one or more cell seeded support matrices are implanted to treat a region comprising a defect, lesion and/or injury. In some embodiments, 1, 2, 3, 4, 5 or more cell seeded support matrices are implanted in a region comprising a defect, lesion and/or injury. In some embodiments, more than one cell seeded support matrix is layered into, or over, a defect, lesion and/or injury.

In some embodiments, a single matrix is utilized to treat multiple defects. In some embodiments, a plurality of defects is treated, each with a different matrix. In some embodiments, one or more defects is treated with a plurality of individual matrices.

In some embodiments, following treatment with a composition of the present disclosure, a region treated (e.g., an articular joint) is evaluated using a screening method (e.g., magnetic resonance imaging). In some embodiments, a treated region is evaluated for filling, repair and/or healing of a defect, lesion and/or injury.

All publications, patent applications, patents and other references mentioned herein are incorporated by reference in their entirety. In addition, the materials, methods and examples are illustrative only and not intended to be limiting. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described herein.

The disclosure is further illustrated by the following examples. The examples are provided for illustrative purposes only. They are not to be construed as limiting the scope or content of the disclosure in any way.

EXAMPLES

Example 1: Knee Cartilage Repair Pre-Clinical Feasibility Study Comparing Autologous and Allogeneic Chondrocyte Sources Combined with Maci Procedure All procedures were conducted after IACUC approval following ASTM F2451-05(2010)1. A total of 18 skeletally mature New Zealand white rabbits were used to compare autologous versus allogeneic chondrocyte sources. An additional 8 rabbits were used for controls (defect only and collagen membrane only, 4 rabbits per group).

For the autologous versus allogeneic study, rabbits were divided into the following cohorts: 1-6: autologous group; 7-12: donors for allogeneic group (non-survival, cartilage harvest only); 13-18: allogeneic group.

Knee cartilage was harvested from rabbits. Collected cartilage tissue was placed in 10 ml Falcon tubes in 0.9% NaCl and transported to Vericel Corporation (Cambridge, MA) for cartilage tissue digestion and cell isolation. Cell-seeded collagen membranes were ready for implantation approximately 3 weeks later. Each sheet contained approximately 500,000-1,000,000 cells per $cm^2$.

NZWR 1-6 received autologous MACI implants on the knee (trochlear groove), while NZWR 13-18 received MACI implants using allogeneic chondrocyte sources. For each rabbit, two 3 mm diameter chondral defects were created in the trochlear groove: one in the superior aspect of the groove, and a second defect in the inferior aspect of the groove, superior to the intercondylar notch. The MACI membrane was cut out using a 3 mm biopsy dermal punch, placed over the defects, and secured using fibrin gel sealant (Tisseel®, Baxter). The patella was carefully relocated into the trochlear groove, the knee capsule was closed using 3-0 Nylon, and dermal tissues were closed using 3-0 Vicryl. After surgery, the rabbits were returned to their cages and kept in an environment with controlled temperature, humidity and circadian cycle, receiving food and water ad libitum. All rabbits were euthanized at 12 weeks. Knees were harvested and processed for histological analysis. Hematoxylin and eosin (H&E), toluidine blue, and collagen type II staining was performed on deparaffinized slides to evaluate neocartilage formation.

All NZWRs reached the 12-week time-point. Results are summarized in FIG. 1. No cartilage regeneration was grossly or histologically visualized in control (defect only group) and membrane-only groups. Only the residuals of collagen membranes were still present in the collagen membrane only group. In the autologous cohort, gross examination revealed defects covered by hyaline-like cartilage tissue. Synovial fluid was clear and present in normal amounts. Histologically, cartilage tissue was characterized by abundant toluidine blue staining. Collagen type II staining matched the glycosaminoglycan (GAG) staining patterns.

At 12 weeks, the neocartilage tissue partially integrated with the surrounding native cartilage tissue. There were no signs of inflammatory infiltrate within the osteochondral tissues. In the allogeneic group, grossly, defects were covered by hyaline-like cartilage tissue. There were no signs of infection or inflammation, and synovial fluid was clear present in normal amounts. Histologically, defects were filled with cartilage tissue that displayed abundant GAG deposition via toluidine blue staining. Collagen staining followed the same staining pattern. Similarly to the autologous group, the neocartilage was partially integrated with the surrounding cartilage. Importantly, no evident immune response including angiogenesis or infiltrating of immunological cells showed in the adjacent tissues.

Example 2: Preparation of Cell Bank Samples

This example demonstrates culturing and freezing cells for long-term storage in a cell bank for use in future subjects.

Before processing, all tissue samples are visually inspected for clarity and accuracy.

If tissue is received in transport media, the media is aspirated away and discarded. If tissue is received in a bag, sterile scissors are used to cut the top corner of the bag. Transport media is aspirated, and then the bag is cut open and pulled apart to create a flat, sterile field. Tissue is transferred to a sterile petri dish and rinsed with Ham's F-12 mixture with L-glutamine (e.g. F-12 solution).

The tissue is weighed and visually inspected for synovium, bone, or any other unwanted tissue by prodding each side to detect any areas that lack rigidity, appear fibrous, or appear fatty. Tissue is trimmed of all bone and synovium so that only cartilage remains. The tissue is then weighed again. If trimmed weight is greater than 9 g, remove excess tissue until the final weight is less than or equal to 9 g. Tissue greater than 9 g or less than 1 g should not be processed.

The weight of the tissue sample is divided by 300 mg to determine how many centrifuge tubes are needed for processing. In each tube, 1× non-specific protease solution is added by adding 5 mL of F-12 solution and 5 mL of 2× protease to each tube. The tissue is divided into pieces weighing between 280 mg and 300 mg and each piece is placed into a sterile petri dish. 0.5 mL of F-12 solution is added to each piece of tissue to ensure the pieces do not dry out. The F-12 solution is aspirated away when ready for protease digestion.

0.5 mL of 1× protease/F-12 solution from each centrifuge tube is added to each petri dish. The tissue is finely minced until all of the pieces are smaller than approximately 0.5 $mm^2$. The minced tissue is transferred to centrifuge tubes comprising 1× protease/F-12 solution. The reactions are incubated at 37° C.±1.5° C. for 75 minutes±15 minutes.

After incubation, the 1× protease/F-12 solution is removed. The tissue pieces are rinsed with 10 mL of F-12 solution. 9 mL of DMEM with L-glutamine, high glucose, and HEPES (e.g. EXXXX solution) and 1 mL of 1% collagenase is added to each centrifuge tube and the reactions are incubated at 37° C.±1.5° C. for 20 hours±4 hours.

10 mL of DMEM with HEPES, glutamax, 20% irradiated Fetal Bovine Serum, and 40 µL/mL gentamicin (e.g. EG2MX solution) is added to each tube. Suspensions from each tube are pooled and centrifuged at 210 RCF for 5 minutes. The supernatant is aspirated away and the pellet is re-suspended in 5 mL EG2MX solution.

Cells are counted for viability using a hemacytometer. Using a microscope, the middle square and each corner square are counted. Viable and non-viable cells are counted and the number of viable cells/mL is calculated. The number of cells needed to prepare to seed at a density of $5\times10^5$ cells/flask in 35 mL of EG2MX solution is determined. Cells are grown in a 5% $CO_2$ incubator at 37° C.±1.5° C.

Primary cells are fed between 3 and 5 days after initiation of culture and in 1 to 4 days intervals afterwards. Conditioned media is poured from each flask into a waste container and 40 mL EG2MX is added into each flask.

Secondary cells are fed between 1 and 4 days after initiation of culture and in 1 to 4 day intervals afterwards.

Prior to cryopreservation, conditioned media is analyzed for quality control. Samples are taken to analyze for sterility.

Example 3: Cryopreservation of Cell Cultures for Storage in Cell Bank

This example demonstrates cryopreservation of allogeneic cell culture for preservation in a cell bank.

Cells are treated with trypsin prior to storage once cells are between 70%±20% confluence or when cultures have reached a maximum of 16 days of growth for primary cultures or 10 days for secondary cultures.

Conditioned media is removed from the flask and then each flask is rinsed with EDTA.

0.05% trypsin and EDTA solution is added to the flask and incubated at 37° C.±1.5° C. until cells are detached, and for no longer than 8 minutes. 10 mL of EG2MX solution is added to deactivate trypsin.

The suspension is centrifuged at 210 RCF for 5 minutes. The supernatant is poured off and the pellet is re-suspended with 3 mL EG2MX.

Cells are counted for viability using a hemacytometer. Using a microscope, the middle square and each corner square are counted. Viable and non-viable cells are counted and the number of viable cells/mL is calculated. The volume needed to prepare a suspension of $10\times10^6$ cells is determined, add that volume of EG2MX is added to the tube. The suspension is now at $5\times10^6$ cells.

The same volume of 20% DMSO as there is volume of suspension is added to each tube. Then, 1 mL of this suspension is added to a cryopreservation vial. The suspension is frozen at −80° C.±10° C. for at least 2 hours, and up to 24 hours.

After initial freeze, cryopreservation vials are transferred to a cryogenic storage dewar comprising liquid nitrogen ($LN_2$).

Example 4: Use of Cell Bank

This example demonstrates thawing of cell bank samples for use in characterization assays and for products.

The frozen cryopreservation vials are placed in a heat block set at 37° C.±1.5° C. for approximately 5 minutes.

Once thawed, the contents are transferred to a new tube. The cryopreservation vial is rinsed with EG2MX solution and transferred to the new tube. The volume is increased to 10 mL with EG2MX.

Cells are counted for viability using a hemacytometer. Using a microscope, the middle square and each corner square are counted. Viable and non-viable cells are counted and the number of viable cells/mL is calculated. The percent of cells recovered after thaw is calculated. The percent recovery should be at least 50%.

To initiate cell culture, 35 mL of EG2MX solution is inoculated with 5 mL of cell suspension in a flask. Cells are grown in a 5% $CO_2$ incubator at 37° C.±1.5° C.

Example 5: Characterization of Cell Bank

This example demonstrates assays used to characterize and/or determine quality of primary (master) cell bank samples prior to use for a product.

After thawing a primary or master cryopreservation vial of cells, cells are counted for viability using a hemacytometer. Using a microscope, the middle square and each corner square are counted. Viable and non-viable cells are counted and the number of viable cells/mL is calculated. The volume of cell suspension needed to achieve $1\times10^5$ cells/mL is calculated. This volume is used for agarose, pellet culture, six well plate, identity/aggrecan, and senescence assays from secondary cultures.

Flasks of $5\times10^5$ and $1\times10^5$ primary cells are prepared for secondary cell culture and grown in a 5% $CO_2$ incubator at 37° C.±1.5° C. Feedings are done between 1 to 4 days after culture initiation. Cells are treated with trypsin as described in Example 3. Trypsin treated cells are used for agarose, pellet culture, and six well plate quality control assays.

Secondary cells are once again counted for viability and flasks with EG2MX are inoculated with cell suspension to obtain $8.0\times10^5$ cells/flask to create a tertiary cell culture. Cells are grown in a 5% $CO_2$ incubator at 37° C.±1.5° C. Tertiary cultures are used to characterize cell bank samples for identity (e.g. presence of chondrocytes) and the presence of aggrecan. The volume of secondary culture suspension needed to achieve $1\times10^6$ cells/tube for agarose testing and six well plate testing is calculated. Tertiary cultures are fed between 1 and 4 days after initiation of culture and in 1 to 4 day intervals afterwards.

For identity and aggrecan testing, cells are loaded onto a membrane. Prior to loading onto a membrane, tertiary cultures are treated with trypsin as described in Example 3. Flasks are pooled and the suspensions are rinsed through a strainer. Cells are counted for viability using a hemacytometer. $20.00\times10^6$ cells in 25 mL are required for membrane loading. The cells are centrifuged at 210 RCF for 5 minutes and the supernatant is removed.

The membrane is placed rough side up in a petri dish and wet with DMEM containing HEPES, high glucose, glutamax, 45 µg/mL gentamicin, and 8.9%±0.2% FBS (e.g. EG1MX solution). The cell pellet is re-suspended in 5 mL of EG1MX, and the volume is brought to a final volume of 25 mL. The membrane is placed in a 5% $CO_2$ incubator at 37° C.±1.5° C. The membrane is packaged 2 to 4 days after loading and rinsed with 15 mL of DMEM with HEPES, without phenol red (e.g. EXXIM).

Flasks of $1\times10^5$ primary cells are prepared for senescence testing and grown in a 5% $CO_2$ incubator at 37° C.±1.5° C. The cells must be treated with trypsin every 7 days as described in Example 3. Feedings occur between every 1 to 4 days after initiation of the culture.

Cells are counted for viability using a hemacytometer. Using a microscope, the middle square and each corner square are counted. Viable and non-viable cells are counted and the number of viable cells/mL is calculated. The volume of cell suspension needed to achieve $1\times10^5$ cells/mL is calculated. Flasks comprising EG2MX solution are inoculated with 1 mL of cells, grown in a 5% $CO_2$ incubator at 37° C.±1.5° C., and population doublings are calculated for each flask, for each passage. PDL=[LOG(cell yield)−LOG(cells inoculated)]/LOG(2). Senescence is reached when the number of population doublings is less than 1 for two weeks in a row.

If the cell bank sample has detectable mycoplasma, is positive for HIV-1, HIV-2, Hepatitis B, Hepatitis C, any other viral contaminants, or does not have a normal human karyotype, the sample will be discarded.

TABLE 1

| Acceptance Criteria for Characterization Tests | |
|---|---|
| Quality Control Test | Acceptance Criteria |
| Tissue type | Intermediate bulk cartilage or normal cartilage |
| Donor screening (CQA) | Meets AATB standards and regulations |
| HIV Type 1 (HIV 1) | Negative or Non-reactive |
| HIV Type 2 (HIV 2) | Negative or Non-reactive |
| Hepatitis B (HBV) | Negative or Non-reactive |
| Hepatitis C (HCV) | Negative or Non-reactive |
| *Treponema pallidum* (syphilis) | Negative or Non-reactive |
| Sterility (primary culture) | No growth detected/observed |
| Endotoxin (primary culture) | Less than or equal to 3 EU/mL |
| Mycoplasma (primary culture) | No detectable mycoplasma |
| Sterility (cell bank vial) | No growth detected/observed |
| Cell viability at primary thaw (cell bank vial) | Greater than or equal to 70% viable cells |
| Six well plate | Average cells/well is greater than or equal to $0.88 \times 10^5$ cells |
| Agarose assay | Greater than or equal to 6.8% of cells forming colonies for greater than or equal to 2 divisions |
| Pellet culture and RTPCR assays | dga greater than or equal to −4.73 Ct and dg2 greater than or equal to −4.54 Ct |
| Senescence | Cultures do not senesce less than 5 passages or are not immortal |
| Identity | d5L greater than or equal to 2.00 Ct |
| Potency | dga Ct greater than or equal to −10.00 Ct |
| Detection of 14 Viruses by RTPCR (Panel I) | No detectable viruses |
| In vitro assay for the presence of porcine viruses | No porcine viruses detected |
| 28-day in vitro assay for the presence of viral contaminants | No viral contaminants detected |

TABLE 1-continued

Acceptance Criteria for Characterization Tests

| Quality Control Test | Acceptance Criteria |
| --- | --- |
| Test for the inapparent viruses | No adenovirus contamination detected |
| Transmission electron microscopic examination of cell cultures | Report results |
| Quantitative product enhanced reverse transcriptase assay for the detection of retrovirus in biological samples | Negative |
| In vitro assay for the presence of bovine viruses | No bovine viruses detected |
| CO1 barcode assay for cell line detection | Identified as human |
| Spectral karyology analysis of human cell lines | Normal human karyotype |

EXEMPLARY EMBODIMENTS

Embodiment 1. A membrane comprising cultured allogeneic human chondrocytes at a density of at least 250,000 cells per $cm^2$, wherein the cultured chondrocytes are derived from cryogenically frozen cell bank samples; and wherein the cultured chondrocytes are characterized by a quality control assay.

Embodiment 2. The composition of embodiment 1, wherein the cell bank comprises human cadaver chondrocytes.

Embodiment 3. The composition of embodiment 1, wherein the cell bank comprises primary cultures.

Embodiment 4. The composition of embodiment 1, wherein the cell bank comprises secondary cultures.

Embodiment 5. The composition of embodiment 1, wherein the quality control assay comprises one or more of agarose, six well plate, and cell pellet assays.

Embodiment 6. A method of preparing a cell bank, the method comprising steps of: obtaining a tissue sample from a human; inspecting the tissue sample for contamination; weighing the tissue sample; mincing the tissue sample; digesting the tissue sample; counting cells in the tissue sample to determine viability; culturing the cells; and cryogenically freezing the cells for storage.

Embodiment 7. The method of embodiment 6 wherein the step of obtaining a tissue sample comprises removing cartilage from a human cadaver.

Embodiment 8. The method of embodiment 6 wherein the step of obtaining a tissue sample comprises removing cartilage from a human cadaver from within about 24 hours to within about 7 days after death.

Embodiment 9. The method of embodiment 6 wherein the step of obtaining a tissue sample comprises removing cartilage from a human cadaver within about 24 hours after death.

Embodiment 10. The method of embodiment 6, wherein the tissue sample is inspected for synovium, bone, fibrous tissue, fatty tissue, and contamination.

Embodiment 11. The method of embodiment 6, wherein the tissue sample weighs from about 1 g to about 9 g.

Embodiment 12. The method of embodiment 6, wherein the tissue sample weighs about 9 g.

Embodiment 13. The method of embodiment 6, wherein the tissue sample is divided into pieces weighing between about 200 mg and about 400 mg.

Embodiment 14. The method of embodiment 6, wherein the tissue sample is divided into pieces weighing between about 200 mg and about 300 mg.

Embodiment 15. The method of embodiment 6, wherein the tissue sample is divided into pieces weighing between about 280 mg and about 300 mg.

Embodiment 16. The method of embodiment 6, wherein the tissue sample is divided into pieces weighing about 300 mg.

Embodiment 17. The method of embodiment 6, wherein the tissue is digested with a protease.

Embodiment 18. The method of embodiment 6, wherein the tissue is digested with collagenase.

Embodiment 19. The method of embodiment 6, wherein the tissue sample is minced into pieces from about 0.5 $mm^2$ to about 3 $mm^2$.

Embodiment 20. The method of embodiment 6, wherein the tissue sample is minced into pieces from about 0.5 $mm^2$ to about 2 $mm^2$.

Embodiment 21. The method of embodiment 6, wherein the tissue sample is minced into pieces from about 0.5 $mm^2$ to about 1 $mm^2$.

Embodiment 22. The method of embodiment 6, wherein the tissue sample is minced into pieces of about 0.5 $mm^2$.

Embodiment 23. The method of embodiment 6, wherein the cells are counted with a hemacytometer.

Embodiment 24. The method of embodiment 6, wherein the tissue sample comprises from about 50% to about 100% viable cells.

Embodiment 25. The method of embodiment 6, wherein the tissue sample comprises from about 70% to about 100% viable cells.

Embodiment 26. The method of embodiment 6, wherein the tissue sample comprises about 70% viable cells.

Embodiment 27. The method of embodiment 6, wherein the cells are cultured in medium comprising DMEM.

Embodiment 28. The method of embodiment 6, wherein the cells are cultured at about 37° C.

Embodiment 29. The method of embodiment 6, wherein the cells are cryogenically frozen at about −80° C. for about 2 to 24 hours.

Embodiment 30. The method of embodiment 6, wherein the cells are cryogenically frozen and stored in liquid nitrogen.

Embodiment 31. A method of characterizing a cell bank sample, the method comprising steps of: thawing cryogenically frozen primary cell bank samples; culturing secondary samples from the primary samples; culturing tertiary samples from the secondary samples; and assaying the samples to determine cell viability, mycoplasma, endotoxin, sterility, senescence, identity, and aggrecan values.

Embodiment 32. A method of characterizing a cell bank sample according to embodiment 31, wherein the samples are assayed using an agarose assay.

Embodiment 33. A method of characterizing a cell bank sample according to embodiment 32, wherein the agarose assay tests for percentage of cells forming colonies for greater than or equal to two divisions.

Embodiment 34. A method of characterizing a cell bank sample according to embodiment 31, wherein an acceptance criterion of the agarose assay comprises at least 6.8% of cells form colonies for at least two divisions.

Embodiment 35. A method of characterizing a cell bank sample according to embodiment 31, wherein the samples are assayed using a six well plate assay.

Embodiment 36. A method of characterizing a cell bank sample according to embodiment 35, wherein the six well plate assay tests for an average number of cells per well.

Embodiment 37. A method of characterizing a cell bank sample according to embodiment 36, wherein an acceptance criterion of the six well assay comprises an average of cells per well that is greater than or equal to $0.88 \times 10^5$.

Embodiment 38. A method of characterizing a cell bank sample according to embodiment 31, wherein the samples are assayed using a pellet culture assay.

Embodiment 39. A method of characterizing a cell bank sample of embodiment 31, wherein the pellet culture assay tests for ability of cells to generate cartilage following cellular culture expansion.

Embodiment 40. A method of characterizing a cell bank sample according to embodiment 39, wherein an acceptance criterion of the pellet culture assay comprises dga greater than or equal to −4.73 Ct.

Embodiment 41. A method of characterizing a cell bank sample of embodiment 31, wherein an acceptance criterion for the assay for mycoplasma comprises no detectable level.

Embodiment 42. A method of characterizing a cell bank sample of embodiment 31, wherein an acceptance criterion for the assay for sterility comprises no detection of growth.

Embodiment 43. A method of characterizing a cell bank sample of embodiment 31, wherein an acceptance criterion for cell viability comprises at least 70% of cells are viable.

Embodiment 44. A method of characterizing a cell bank sample of embodiment 31, wherein an acceptance criterion for senescence comprises cultures do not senesce in less than 5 passages or cultures are not immortal.

Embodiment 45. A method of characterizing a cell bank sample of embodiment 31, wherein an acceptance criterion for identity comprises identification of the presence of chondrocytes.

Embodiment 46. A method of culturing a cell bank sample, the method comprising steps of: thawing a cryogenically frozen cell bank sample; adding culture medium to a flask; counting cells to determine viability; growing the cells and the medium in a cell culture; feeding the cell culture; and treating the cell culture with trypsin.

Embodiment 47. The method of culturing a cell bank sample of embodiment 46, wherein the cryogenically frozen cell bank sample is thawed in a water bath, a heat block, or a dry cell bath at about 37° C.

Embodiment 48. The method of embodiment 46, wherein the sample is cultured in medium comprising DMEM.

Embodiment 49. The method of embodiment 46, wherein the cells are counted with a hemacytometer.

Embodiment 50. The method of embodiment 46, wherein the cell culture is fed at least every 1 to 4 days.

Embodiment 51. The method of embodiment 46, wherein the cell culture is treated with 0.05% trypsin solution.

Embodiment 52. The method of embodiment 46, wherein the cell culture is treated with trypsin solution until the cells are detached from the flask.

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A composition comprising:
   cultured allogeneic cells comprising chondrocytes grown from a cryogenically frozen cell bank sample; and
   a resorbable collagen membrane comprising a combination of type I and type III porcine collagen derived from porcine peritoneum;
     wherein the cultured allogeneic cells are seeded on the resorbable collagen membrane at a density of at least 250,000 cells per cm$^2$,
     wherein the allogeneic cells are arranged in a monolayer on the resorbable collagen membrane, and
     wherein the allogeneic cells are dedifferentiated.

2. A method of manufacturing an allogeneic cartilage matrix, the method comprising steps of:
   thawing a cryogenically frozen cell bank sample comprising chondrocytes;
   culturing the cells of the sample;
   characterizing the sample;
   preparing a resorbable collagen membrane;
   seeding the resorbable collagen membrane with the cultured cells; and
   packaging the resorbable collagen membrane,
   wherein characterizing the sample comprises characterizing the sample by one or more control assays comprising:
   an agarose assay comprising an acceptance criterion comprising at least 6.8% of cells forming colonies for at least two divisions.

3. The composition of claim 1, wherein the allogeneic cells are configured to be implanted to treat a chondral defect and/or an osteochondral defect.

4. The composition of claim 3, wherein the allogeneic cells comprise cultured allogeneic cells grown from a cryogenically frozen cell bank sample, and
   wherein the cryogenic cell bank sample is thawed in a water bath, a heat block, or a dry cell bath at about 37° C.

5. The composition of claim 4, wherein the cultured allogeneic cells are cultured in medium comprising DMEM.

6. The composition of claim 4, wherein the cultured allogeneic cells are characterized for sterility, endotoxin, mycoplasma, senescence, identity, aggrecan, and/or karyology.

7. The method of claim 2, wherein the matrix comprises dedifferentiated cells, wherein the density of cells seeded on the resorbable collagen membrane is at least 250,000 cells per cm$^2$, and
wherein the matrix is coated with an adhesive agent.

8. The composition of claim 1, wherein the cultured allogeneic cells comprise chondrocytes,
wherein the chondrocytes comprise human chondrocytes that are (1) expanded in culture, and (2) seeded onto the resorbable collagen membrane, and
wherein the composition comprises one or more chondrocyte markers and one or more non-chondrocyte markers, the non-chondrocyte markers comprising at least one of a fibroblast marker and a synoviocyte marker.

9. The composition of claim 8, wherein the support matrix comprises at least 70% of viable cells, and
wherein the composition comprises less than about 10 µg/ml of fetal bovine serum albumin.

10. The composition of claim 8, wherein the chondrocytes in the cell bank comprise tissue harvested from an adult human or tissue harvested from a cadaver.

11. The composition of claim 10, wherein the tissue comprises chondrocyte precursors.

12. The composition of claim 1, wherein the composition comprises at least one surface seeded with allogeneic human chondrocytes.

13. The method of claim 2, wherein culturing the cells of the sample comprises culturing the cells at temperatures between 31° C. and 37° C., with a $CO_2$ content between 2% and 10%, and an oxygen content between 1% and 22%.

14. The method of claim 2, wherein the one or more control assays comprises analyzing cells for bacterial endotoxins comprising an acceptance criterion of less than or equal to 3 EU/mL.

15. The method of claim 2, wherein the one or more control assays comprises an acceptance criterion for senescence comprising cultures that do not senesce in less than 5 passages.

16. The method of claim 2, wherein the one or more control assays comprises a pellet culture assay comprising an acceptance criterion comprising:
dga greater than or equal to −4.73 Ct; and
dg2 greater than or equal to −4.54 Ct.

17. The composition of claim 1, wherein the cultured allogeneic cells are seeded on the resorbable collagen membrane at a density of at least $1.5 \times 10^7$ cells per cm$^2$.

18. A composition comprising:
cultured allogeneic cells comprising chondrocytes grown from a cryogenically frozen cell bank sample; and
a resorbable collagen membrane comprising a combination of type I and type III porcine collagen derived from porcine peritoneum, the resorbable collagen membrane being coated with a fibrin adhesive;
wherein the cultured allogeneic cells are seeded on the resorbable collagen membrane at a density of at least 250,000 cells per cm$^2$,
wherein the allogeneic cells are dedifferentiated, and
wherein the composition comprises at least one of a chondrocyte marker and a non-chondrocyte marker.

19. The method of claim 18, wherein the dedifferentiated allogeneic cells:
exhibit a fibroblastic phenotype;
down regulate expression of a gene encoding ECM; and/or
produce and/or secrete a lesser amount of at least one of collagen and aggrecan.

* * * * *